(12) United States Patent
Griesgraber

(10) Patent No.: US 10,414,779 B2
(45) Date of Patent: Sep. 17, 2019

(54) FUSED [1,2]IMIDAZO[4,5-C] RING COMPOUNDS SUBSTITUTED WITH GUANIDINO GROUPS

(71) Applicant: 3M INNOVATIVE PROPERTIES COMPANY, St. Paul, MN (US)

(72) Inventor: George W. Griesgraber, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/327,404

(22) PCT Filed: Aug. 1, 2017

(86) PCT No.: PCT/US2017/044799
§ 371 (c)(1),
(2) Date: Feb. 22, 2019

(87) PCT Pub. No.: WO2018/038877
PCT Pub. Date: Mar. 1, 2018

(65) Prior Publication Data
US 2019/0194226 A1 Jun. 27, 2019

Related U.S. Application Data

(60) Provisional application No. 62/379,776, filed on Aug. 26, 2016.

(51) Int. Cl.
C07D 498/14 (2006.01)
C07D 498/22 (2006.01)
A61P 37/04 (2006.01)

(52) U.S. Cl.
CPC ............ *C07D 498/14* (2013.01); *A61P 37/04* (2018.01); *C07D 498/22* (2013.01)

(58) Field of Classification Search
CPC .......................... C07D 498/14; C07D 498/22
See application file for complete search history.

(56) References Cited

U.S. PATENT DOCUMENTS

| | | | |
|---|---|---|---|
| 4,689,338 | A | 8/1987 | Gerster |
| 5,352,784 | A | 10/1994 | Nikolaides |
| 5,446,153 | A | 8/1995 | Lindstrom |
| 6,039,969 | A | 3/2000 | Tomai |
| 6,110,929 | A | 8/2000 | Gerster |
| 6,194,425 | B1 | 2/2001 | Gerster |
| 6,200,592 | B1 | 3/2001 | Tomai |
| 6,331,539 | B1 | 12/2001 | Crooks |
| 6,451,810 | B1 | 9/2002 | Coleman |
| 6,664,264 | B2 | 12/2003 | Dellaria |
| 7,544,697 | B2 | 6/2009 | Hays |
| 7,888,349 | B2 | 2/2011 | Kshirsagar |
| 7,906,506 | B2 | 3/2011 | Griesgraber |
| 7,915,281 | B2 | 3/2011 | Moser |
| 7,943,609 | B2 | 5/2011 | Griesgraber |
| 8,034,938 | B2 | 10/2011 | Griesgraber |
| 8,088,788 | B2 | 1/2012 | Kshirsagar |
| 8,088,790 | B2 | 1/2012 | Kshirsagar |
| 8,207,162 | B2 | 6/2012 | Griesgraber |
| 8,350,034 | B2 | 1/2013 | Griesgraber |
| 8,546,383 | B2 | 10/2013 | Griesgraber |
| 8,673,932 | B2 | 3/2014 | Kshirsagar |
| 8,691,837 | B2 | 4/2014 | Krepski |

(Continued)

FOREIGN PATENT DOCUMENTS

| | | |
|---|---|---|
| WO | WO 2005-051380 | 6/2005 |
| WO | WO 2006-074003 | 7/2006 |
| WO | WO 2006-086633 | 8/2006 |

(Continued)

OTHER PUBLICATIONS

Berge, "Pharmaceutical Salts"; Journal of Pharmaceutical Sciences, 1977, vol. 66, No. 1, pp. 1-19.

Bernatowicz, "1H-Pyrazole-a-carboxamidine Hydrochloride: An Attractive Reagent for Guanylation of Amines and Its Application to Peptide Synthesis," Journal of Organic Chemistry, 1992, vol. 57, pp. 2497-2502.

Bernatowicz, "Urethane Protected Derivatives of 1-Guanylpyrazole for the Mild and Efficient Preparation of Guanidines," Tetrahedron Letters, 1993, vol. 34, No. 21, pp. 3389-3392.

Katritzky, "Recent Developments in Guanylating Agents," ARKIVOC; 2005 (iv) pp. 49-87.

(Continued)

*Primary Examiner* — Laura L Stockton
(74) *Attorney, Agent, or Firm* — Eric E. Silverman

(57) ABSTRACT

Fused [1,2]Imidazo[4,5-c] ring compounds (e.g., imidzao[4,5-c]quinolines, 6,7,8,9-tetrahydroimidazo[4,5-c]quinolines, imidazo[4,5-c]naphthyridines, and 6,7,8,9-tetrahydroimidazo[4,5-c]naphthyridines) substituted on the fused ring with a group that contains a guanidine or substituted guanidine moiety, pharmaceutical compositions containing the compounds, and methods of making the compounds are disclosed. Methods of use of the compounds as immune response modifiers, for inducing cytokine biosynthesis in animals and in the treatment of diseases including viral and neoplastic diseases are also disclosed.

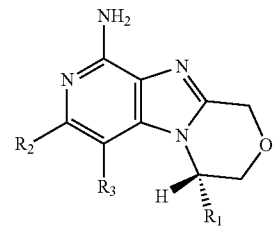

Formula I

23 Claims, No Drawings

(56) References Cited

U.S. PATENT DOCUMENTS 8,697,873 B2    4/2014   Krepski

FOREIGN PATENT DOCUMENTS

| WO | WO 2008-008432 | 1/2008 |
| WO | WO 2017-040233 | 3/2017 |
| WO | WO 2017-040234 | 3/2017 |

OTHER PUBLICATIONS

Lee, "1*H*-Pyrazole-1-Carboxamidines: New Inhibitors of Nitric Oxide Synthase," Biorganic & Medicinal Chemistry Letters, 2000, vol. 10, pp. 2771-2774.

Lee, "Solid-Phase Syntheses of $N^\omega$-Propylarginine-Containing Dipeptides, Dipeptide Esters, and Dipeptide Amides," Synthesis, 1999, (Special Issue), pp. 1495-1499.

Maryanoff, "A Convenient Synthesis of Guanidines from Thioureas," Journal of Organic Chemistry, 1986, vol. 51, No. 10, pp. 1882-1884.

Zhang, "Recent Development of Synthetic Preparation Methods for Guanidines via Transition Metal Catalysis"; Chemical Communications, 2015, vol. 51, No. 2, pp. 254-265.

International Search Report for PCT International Application No. PCT/US2017/044799, dated Sep. 26, 2017, 5 pages.

FUSED [1,2]IMIDAZO[4,5-C] RING COMPOUNDS SUBSTITUTED WITH GUANIDINO GROUPS

CROSS REFERENCE TO RELATED APPLICATIONS

This application is a national stage filing under 35 U.S.C. 371 of PCT/US2017/044799, filed Aug. 1, 2017, which claims the benefit of U.S. Provisional Application No. 62/379,776, filed Aug. 26, 2016.

BACKGROUND

Some drug compounds act by stimulating certain key aspects of the immune system, as well as by suppressing certain other aspects (e.g., U.S. Pat. Nos. 6,039,969 and 6,200,592). These compounds are sometimes referred to as immune response modifiers (IRMs). Some IRM compounds are useful for treating viral diseases, neoplasias, and $T_H2$-mediated diseases; some are useful as vaccine adjuvants.

IRM compounds have been reported based on the following bicyclic and tricyclic ring systems: 1H-imidazo[4,5-c]quinolin-4-amines (e.g., U.S. Pat. No. 4,689,338); 1H-imidazo[4,5-c]pyridin-4-amines (e.g., U.S. Pat. No. 5,446,153); 1H-imidazo[4,5-c][1,5]naphthyidin-4-amines (e.g., U.S. Pat. No. 6,194,425); thiazolo[4,5-c]quinolone-4-amines and oxazolo[4,5-c]quinolone-4-amines (e.g., U.S. Pat. No. 6,110,929); 6,7,8,9-1H-tetrahydro-1H-imidazo[4,5-c]quinolin-4-amines (e.g., U.S. Pat. No. 5,352,784); 2H-pyrazolo[3,4-c]quinoline-4-amines (e.g., U.S. Pat. No. 7,544,697); and N-1 and 2-substituted 1H-imidazo[4,5-c]quinolin-4-amines (e.g., U.S. Pat. Nos. 6,331,539, 6,451,810, 6,664,264, 8,691,837, 8,088,790, 8,673,932, 8,697,873, 7,915,281).

SUMMARY

New compounds that can be useful in inducing cytokine biosynthesis in animals are disclosed. Such compounds are of the following Formulas I, VII, and IX:

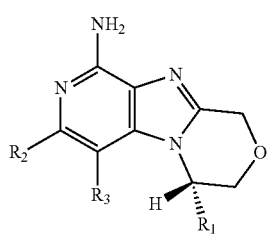

Formula I

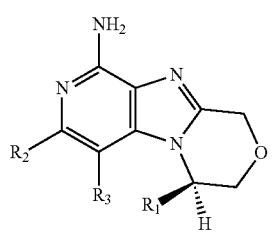

Formula VII

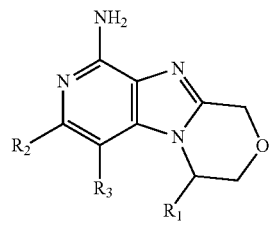

Formula IX wherein $R_1$, $R_2$, $R_3$, are as defined below. A common structural feature of the compounds of Formulas I, VII, and IX is the inclusion of a guanidine group or substituted guanidine group as a component of $R_1$.

In addition, more specific examples of such compounds include the compounds of Formulas II-V which are defined below, as well as salts, particularly pharmaceutically acceptable salts, thereof.

The compounds and salts, such as pharmaceutically acceptable salts, of Formulas I-X can be useful as immune response modifiers due to their ability to induce cytokine biosynthesis (e.g., induce the synthesis of at least one cytokine) and otherwise modulate the immune response when administered to animals. The compounds can therefore be useful in the treatment of a variety of conditions such as viral diseases and tumors that are responsive to such changes in the immune response.

Pharmaceutical compositions containing an effective amount of one or more compounds of Formulas I-X and salts, particularly pharmaceutically acceptable salts, thereof are disclosed. Also disclosed are methods of inducing cytokine biosynthesis in an animal, treating a viral disease in an animal, and treating a neoplastic disease in an animal by administering to the animal one or more compounds from Formulas I-X and/or pharmaceutically acceptable salts thereof.

Methods for synthesizing compounds of Formulas I-X are provided.

The above summary of the present disclosure is not intended to describe each disclosed embodiment or every implementation of the disclosure. The description that follows more particularly exemplifies illustrative embodiments. In several places throughout the description, guidance is provided through lists of examples, which can be used in various combinations. In each instance, the recited list serves only as a representative group and should not be interpreted as an exhaustive list.

DETAILED DESCRIPTION

As used herein, "a", "an", "the", "at least one", and "one or more" are used interchangeably and are intended to include both the singular and the plural except in cases where the singular alone is specifically called for or clearly required by the context.

As used herein, "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

"Ph" is used as an abbreviation for a phenyl group.

As used herein, "pharmaceutically acceptable carriers" include those carriers that can deliver therapeutically effective amounts of one or more of the compounds or salts of the disclosure to a subject by a chosen route of administration, are generally tolerated by the subject, and have an acceptable toxicity profile (preferably minimal to no toxicity at an administered dose). Some suitable pharmaceutically acceptable carriers are described in Remington's Pharmaceutical Sciences, 18$^{th}$ Edition (1990), Mack Publishing Co. and can be readily selected by one of ordinary skill in the art.

"Therapeutically effective amount" and "effective amount" are defined as an amount of compound or salt sufficient to induce a therapeutic or prophylactic effect, such a cytokine induction, immunomodulation, antitumor activity, and/or antiviral activity.

"Independently," when used to describe the identity of one or more variable reference elements (such as when used in the phrase "independently selected" or "independently selected from the group"), means that each occurrence of any of the variable elements may have the same or different identity, within the specified limitations, regardless of the identity of any other occurrence of the reference element(s). Thus, if there are two occurrences of reference element "A," and reference element "A" can be independently selected from identity "B" or identity "C", each of the two occurrences of "A" can be either "B" or "C", in any combination (e.g., "B,B"; "B,C"; "C,B"; or "C,C"). Alternatively, if there are two different reference elements (reference element "D" and reference element "E") that can occur together and reference element "D" and reference element "E" can each be independently selected from identity "F" or identity "G", then each occurrence of "D" can be "F" or "G" and likewise each occurrence of "E" can be "F" or "G", to produce any combination of "D" and "E" (e.g., "D"="F" and "E"="F"; "D"="F" and "E"="G"; "D"="G" and "E"="F"; or "D"="G" and "E"="G".

The terms "alkyl", "alkenyl", "alkynyl" and the prefix "alk-" are inclusive of straight chain groups, branched chain groups, cyclic groups, and combinations thereof, e.g. cycloalkyl and cycloalkenyl. Alkyl groups are saturated aliphatic hydrocarbons. Alkenyl groups are unsaturated aliphatic hydrocarbons having one or more carbon-carbon double bonds. Alkynyl groups are unsaturated aliphatic hydrocarbons having one or more carbon-carbon triple bonds. Unless otherwise specified, these groups contain from 1 to 14 carbon atoms, with alkenyl groups containing from 2 to 14 carbon atoms and alkynyl groups containing from 2-14 atoms. In some embodiments, these groups have a total of up to 14 carbon atoms, up to 12 carbon atoms, up to 10 carbon atoms, up to 8 carbon atoms, up to 6 carbon atoms, up to 5 carbon atoms, up to 4 carbon atoms, up to 3 carbon atoms, or up to 2 carbon atoms. In some embodiments, these groups have at least 1 carbon atom, at least 2 carbon atoms, at least 3 carbon atoms, or at least 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, norbornenyl, and the like The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, pentafluoroethyl and the like.

Unless otherwise specified, "alkylene", "alkenylene", and "alkynylene" are the diradical equivalents of the "alkyl", "alkenyl", and "alkynyl" defined above. The terms, "alkylenyl", "alkenylenyl", and "alkynylenyl" are used when "alkylene", "alkenylene", and "alkynylene" respectively, are substituted. For example, an alkoxyalkylenyl group comprises an alkylene moiety to which an alkoxy group is attached (e.g., —CH$_2$OCH$_3$, —CH$_2$CH$_2$OCH$_3$, —CH$_2$OCH$_2$CH$_3$, etc.). As a further example, a hydroxyalkylenyl group comprises an alkylene moiety to which a hydroxy group is attached (e.g., —CH$_2$OH, —CH$_2$CH$_2$OH, etc.). As yet another example arylalkylenyl group comprises an alkylene moiety to which an aryl group is attached [e.g., —CH$_2$Ph, —CH$_2$CH$_2$Ph, etc.].

An alkylene group with carbon atoms optionally "interrupted" by one or more —O— groups refers to having carbon atoms on either side of the —O—. Examples include —CH$_2$CH$_2$—O—CH$_2$CH$_2$—, —CH$_2$—CH$_2$—O—CH$_2$—CH$_2$—O—CH$_2$CH$_2$—, —(CH$_2$)$_{2-4}$—(OCH$_2$CH$_2$-)$_{1-5}$, —(CH$_2$)$_{2-6}$—(OCH$_2$CH$_2$-)$_{1-4}$, etc.

Some examples of alkylamino groups include —NHCH$_3$, —NHCH$_2$CH$_3$, —NHCH(CH$_3$)$_2$, etc. It is understood that the two alkyl groups of a dialkylamino group can be the same or different alkyl groups. Some examples of dialkylamino groups include —N(CH$_3$)$_2$, —N(CH$_2$CH$_3$)$_2$, —N(CH$_3$)(CH$_2$CH$_3$), —N(CH$_3$)(CH$_2$CH$_2$CH$_3$), etc.

Some examples of alkylaminoalkylenyl groups include —CH$_2$NHCH$_3$, —CH$_2$NHCH$_2$CH$_3$, —CH$_2$CH$_2$NHCH$_3$, etc.

Some examples of benzyloxyalkylenyl groups include —CH$_2$OCH$_2$Ph, —CH$_2$CH$_2$OCH$_2$Ph, —CH$_2$CH$_2$CH$_2$OCH$_2$Ph, etc.

Some examples of —C(O)Oalkyl include —C(O)OCH$_3$, —C(O)OCH$_2$CH$_3$, —C(O)OCH$_2$CH$_2$CH$_3$, —C(O)OC(CH$_3$)$_3$, etc.

The term "aryl" as used herein includes carbocyclic aromatic rings or ring systems. Examples of aryl groups include phenyl (designated by the abbreviation "Ph" herein), naphthyl, and biphenyl.

The term "heteroaryl" includes aromatic rings or ring systems that contain at least one ring heteroatom (e.g. O, S, N). In some embodiments, the term "heteroaryl" includes a ring or ring system that contains 2-12 carbon atoms, 1-3 rings, 1-4 heteroatoms, with O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, quinoxalinyl, benzothiazolyl, napthyridinyl, ixoxazolyl, isothiazolyl, purinyl, quinazolinyl, pyrazinyl, 1-oxidopyridyl, pyridazinyl, triazinyl, tetrazinyl, oxadiazolyl, thiadiazolyl, and the like. Preferred heteroaryl groups include, thienyl, pyridyl, quinolinyl, indolyl and imidazolyl.

The terms "arylene", "-arylene-", "heteroarylene", and "-heteroarylene-" are the diradical equivalents of the "aryl" and "heteroaryl" groups defined above. The terms "arylenyl" and "heteroarylenyl" are used when "arylene" and "heteroarylene" are substituted. For example an alkylarylenyl group comprises an arylene moiety to which an alkyl group is attached (e.g., -Ph-CH$_3$).

The term "compound" includes not only the specific structural formula as drawn or named, but also its configurational isomers, stereoisomers, such as enantiomers, diastereomers, and meso isomers, as well as combinations of one or more of any of the foregoing, except in cases when a specific isomer, enantiomer, or the like is specifically called out. For those structures that exist as tautomers, the term "compound" is intended to include all tautomers, even when only one is drawn, unless only a single tautomer is explicitly recited The "salt" of a compound includes pharmaceutically acceptable salts, such as those described in Berge, Stephen M., "Pharmaceutical Salts", *Journal of Pharmaceutical Sciences,* 1977, 66, pages 1-19. For example, salts can be prepared by reacting a free base compound (that is, one not in a salt form) with an inorganic or organic acid such as, for example, hydrochloric acid, sulfuric acid, hydrobromic acid, methane sulfonic acid, ethane sulfonic acid, malic acid, maleic acid, acetic acid, trifluoroacetic acid, para-toluenesulfonic acid, salicylic acid, succinic acid, tartaric acid, citric acid, pamoic acid, xinafoic acid, oxalic acid, and the like. Typical pharmaceutically acceptable salts include hydrochloride and dihydrochloride.

This disclosure provides compounds of the following Formula I:

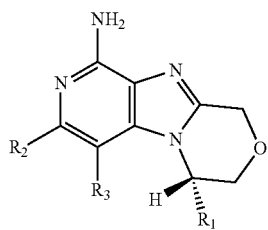

Formula I wherein $R_1$, $R_2$, and $R_3$ are as defined below; and pharmaceutically acceptable salts thereof.

Examples of compounds of Formula I are more specifically defined by the following Formulas II-V:

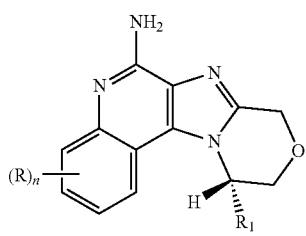

Formula II

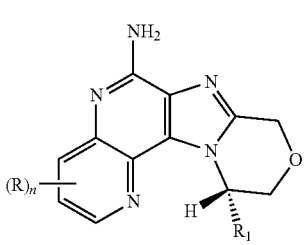

Formula III

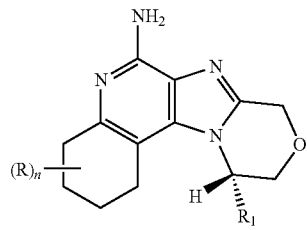

Formula IV

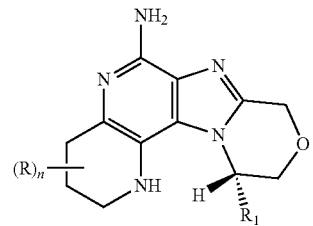

Formula V wherein R, $R_1$, and n are as defined below as well as salts, particularly pharmaceutically acceptable salts, thereof.

For compounds and salts, such as pharmaceutically acceptable salts, of Formula I, $R_2$ and $R_3$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R groups.

For compounds and salts, such as pharmaceutically acceptable salts, of Formulas I-V:
R is selected from the group consisting of halogen, hydroxy, alkyl, alkoxy, haloalkyl, —C(O)Oalkyl, —C(O)OCH$_2$Ph, —C(O)Oaryl, amino, alkylamino, dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxy, hydroxyalkylenyl, alkoxyalkylenyl, arylalkyleneoxy, nitrile, amino, alkylamino, and dialkylamino;
n is an integer from 0 to 2;
$R_1$ is —X—N($R_4$)—C(=N—$R_5$)—N(H)$R_6$;
X is selected from the group consisting of alkylene, alkenylene, and alkynylene, wherein any of the alkylene, alkenylene, and alkynylene groups can be optionally interrupted by one or more —O— groups;
$R_4$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents independently selected from the group consisting of halogen, hydroxy, alkyl, alkoxy, haloalkyl, and nitrile;
$R_5$ and $R_6$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, benzyloxyalkylenyl, and —C(O)Oalkyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxy, alkoxy, alkyl, haloalkyl, cycloalkyl, nitrile, aryl, heteroaryl, and dialkylamino.

In some embodiments of Formula I, $R_2$ and $R_3$ are taken together to form a fused benzene ring, a fused pyridine ring, or a fused cyclohexene ring.

In some embodiments of Formula I, $R_2$ and $R_3$ are taken together to form a fused benzene ring or a fused cyclohexene ring.

In some embodiments of Formula I, $R_2$ and $R_3$ are taken together to form a fused benzene ring or a fused pyridine ring.

In some embodiments of Formula I, $R_2$ and $R_3$ are taken together to form a fused benzene ring.

In some embodiments of Formula I, $R_2$ and $R_3$ are taken together to form a fused benzene ring, a fused pyridine ring, or a fused cyclohexene ring; wherein the fused benzene ring, fused pyridine ring, or fused cyclohexene ring is either unsubstituted or substituted by one and only one R group.

In some embodiments of Formula I, $R_2$ and $R_3$ are taken together to form a fused benzene ring or a fused pyridine ring; wherein the fused benzene ring or fused pyridine ring is either unsubstituted or substituted by one and only one R group.

In some embodiments of Formulas II-V, n is 0 or 1.

In some embodiments of Formulas II-V, n is 0.

In some embodiments of Formulas I-V, R is selected from the group consisting of hydroxy, F, Cl, Br, —$CF_3$, —O—$C_{1-6}$ alkyl, and —$C_{1-6}$ alkyl.

In some embodiments of Formulas I-V, R is selected from the group consisting of hydroxy, F, Cl, Br, —$CF_3$, —$OCH_3$, —$OCF_3$, —$OCH_2CH_3$, —$OCH(CH_3)_2$, —$CH_3$, —$CH_2CH_3$, —$CH_2CH_2CH_3$, and —$CH(CH_3)_2$.

In some embodiments of Formulas I-V, R is —$C(O)OC_{1-4}$ alkyl.

In some embodiments of Formulas I-V, R is selected from the group consisting of —$CO_2CH_3$, —$CO_2CH_2CH_3$, —$CO_2CH(CH_3)_2$, —$CO_2CH_2CH_2CH_3$, —$CO_2CH_2CH_2CH_2CH_3$, —$CO_2$—$CH_2Ph$, and —$CO_2CH_2CH(CH_3)_2$.

In some embodiments of Formulas I-V, R is selected from the group consisting of halogen, hydroxy, alkyl, alkoxy, haloalkyl, —C(O)Oalkyl, —$C(O)OCH_2Ph$, —C(O)Oaryl, amino, alkylamino, and dialkylamino.

In some embodiments of Formulas I-V, R is selected from the group consisting of alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxy, hydroxyalkylenyl, alkoxyalkylenyl, arylalkyleneoxy, nitrile, amino, alkylamino, and dialkylamino.

In some embodiments of Formulas I-V, R is selected from the group consisting of aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy.

In some embodiments of Formulas I-V, $R_4$ is hydrogen, $C_{1-8}$alkyl, or —$CH_2Ph$.

In some embodiments of Formulas I-V, $R_4$ is hydrogen or $C_{1-4}$ alkyl.

In some embodiments of Formulas I-V, $R_4$ is hydrogen.

In some embodiments of Formulas I-V, $R_4$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_3$, —$CH_2CH_2CH(CH_3)_2$, cyclopentyl, cyclohexyl, —$CH_2$(cyclopentyl), —$CH_2$(cyclohexyl), and —$CH_2CH_2$—O—$CH_3$.

In some embodiments of Formulas I-V, $R_4$ is selected from the group consisting of hydrogen, alkyl, —$CH_2Ph$, —$CH_2CH_2Ph$, —$CH_2CH_2$—O-Ph, —$CH_2CH_2$—O—$CH_2Ph$, and —$(CH_2)_{2-6}$—O—$(CH_2)_{1-6}Ph$, wherein Ph can be either unsubstituted or substituted with one or more substituents independently selected from the group consisting of halogen, hydroxy, alkyl, alkoxy, haloalkyl, and nitrile.

In some embodiments of Formulas I-V, X is alkylene optionally interrupted by one or more —O— groups.

In some embodiments of Formulas I-V, X is a $C_{2-12}$ alkylene optionally interrupted by one or more —O— groups.

In some embodiments of Formulas I-V, X is $C_{2-8}$ alkylene.

In some embodiments of Formulas I-V, X is $C_{2-6}$ alkylene.

In some embodiments of Formulas I-V, X is $C_{2-5}$ alkylene.

In some embodiments of Formulas I-V, X is a $C_{2-8}$ alkylene optionally interrupted by one or more —O— groups.

In some embodiments of Formulas I-V, X is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2$—O—$CH_2CH_2$—, —$CH_2CH_2$—O—$CH_2CH_2$.

In some embodiments of Formulas I-V, $R_5$ and $R_6$ are independently selected from the group consisting of hydrogen, alkyl, phenyl, and phenylalkylenyl.

In some embodiments of Formulas I-V, $R_5$ and $R_6$ are independently selected from the group consisting of hydrogen, alkyl, cycloalkyl, cycloalkylalkylenyl, aryl, and arylalkylenyl.

In some embodiments of Formulas I-V, $R_5$ and $R_6$ are independently selected from the group consisting of alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, benyloxyalkylenyl groups can be either unsubstituted or substituted with one or more substituents independently selected from the group consisting of halogen, hydroxy, alkoxy, alkyl, haloalkyl, cycloalkyl, nitrile, aryl, heteroaryl, and dialkylamino.

In some embodiments of Formulas I-V, $R_5$ and $R_6$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$CH_2CH_2$—O—$CH_3$, —$(CH_2)_{3-8}$—O—$CH_3$, and —$CH_2CH_2CH_2N(CH_3)_2$.

In some embodiments of Formulas I-V, $R_5$ and $R_6$ are independently selected from the group consisting of hydrogen, alkyl, -Ph, —$CH_2Ph$, —$CH_2CH_2Ph$, —$(CH_2)_{3-8}Ph$, —CH$_2$CH$_2$—O-Ph, —(CH$_2$)$_{3-8}$OPh, —CH$_2$CH$_2$—O—CH$_2$Ph, —(CH$_2$)$_{3-8}$OCH$_2$Ph, and —(CH$_2$)$_{2-8}$—O—(CH$_2$)$_{1-4}$Ph, wherein the Ph group can be either unsubstituted or substituted with one or more substituents independently selected from the group consisting of halogen, hydroxy, alkoxy, alkyl, haloalkyl, cycloalkyl, and nitrile.

In some embodiments of Formulas I-V, R$_5$ and R$_6$ are independently selected from the group consisting of hydrogen and —C(O)Oalkyl.

In some embodiments of Formulas I-V, R$_5$ is alkyl and R$_6$ is alkyl.

In some embodiments of Formulas I-V, R$_5$ is C$_{1-8}$alkyl and R$_6$ is C$_{1-8}$alkyl.

In some embodiments of Formulas I-V, R$_5$ is C$_{1-4}$ alkyl and R$_6$ is C$_{1-4}$ alkyl.

In some embodiments of Formulas I-V, R$_5$ is —C(O)OC(CH$_3$)$_3$ and R$_6$ is —C(O)OC(CH$_3$)$_3$.

In some embodiments of Formulas I-V, R$_5$ is hydrogen and R$_6$ is hydrogen.

In some embodiments of Formulas I-V, R$_4$ is hydrogen; R$_5$ is hydrogen; and R$_6$ is hydrogen.

In some embodiments of Formulas II-V, X is alkylene optionally interrupted by one or more —O— groups; n is 0 or 1; R is selected from the group consisting of halogen, hydroxy, alkyl, alkoxy, and haloalkyl.

In some embodiments of Formulas I-V, X is alkylene.

In some embodiments of Formulas I-V, X is alkylene optionally interrupted by one or more —O— groups; R$_5$ and R$_6$ are independently selected from the group consisting of hydrogen and alkyl.

In some embodiments of Formulas I-V, X is alkylene optionally interrupted by one or more —O— groups; R$_5$ is alkyl; R$_6$ is alkyl.

In some embodiments of Formulas I-V, X is alkylene; R$_5$ is alkyl; R$_6$ is alkyl.

In some embodiments of Formulas I-V, X is alkylene optionally interrupted by one or more —O— groups; R$_5$ is hydrogen; and R$_6$ is hydrogen.

In some embodiments of Formulas I-V, X is alkylene; R$_5$ is hydrogen; and R$_6$ is hydrogen.

In some embodiments of Formulas I-V, X is alkylene optionally interrupted by one or more —O— groups; R$_4$ is hydrogen; R$_5$ is hydrogen; and R$_6$ is hydrogen.

In some embodiments of Formulas I-V, X is alkylene; R$_4$ is hydrogen; R$_5$ is hydrogen; and R$_6$ is hydrogen.

This disclosure also provides compounds of the following Formula VI:

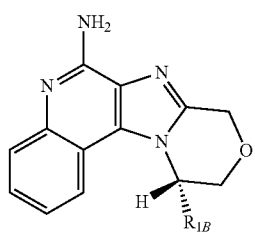

Formula VI wherein R$_{1B}$, is as defined below; as well as salts thereof, which are typically pharmaceutically acceptable salts.

For compounds and salts, such as pharmaceutically acceptable salts, of Formula VI:

R$_{1B}$ is —X$_B$—N(R$_{4B}$)—C(=N—R$_{5B}$)—N(H)R$_{6B}$,

X$_B$ is selected from the group consisting of alkylene, alkenylene, and alkynylene, wherein the alkylene, alkenylene, and alkynylene groups can be optionally interrupted by one or more —O— groups;

R$_{4B}$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl; wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents independently selected from the group consisting of halogen, hydroxy, alkyl, alkoxy, haloalkyl, and nitrile;

R$_{5B}$ and R$_{6B}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, benzyloxyalkylenyl, and —C(O)Oalkyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxy, alkoxy, alkyl, haloalkyl, cycloalkyl, nitrile, aryl, heteroaryl, and dialkylamino.

In some embodiments of Formula VI, R$_{4B}$ is hydrogen, C$_{1-8}$alkyl, or —CH$_2$Ph.

In some embodiments of Formula VI, R$_{4B}$ is hydrogen or C$_{1-4}$ alkyl.

In some embodiments of Formula VI, R$_{4B}$ is hydrogen.

In some embodiments of Formula VI, R$_{4B}$ is selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$CH$_2$CH(CH$_3$)$_2$, cyclopentyl, cyclohexyl, —CH$_2$(cyclopentyl), —CH$_2$(cyclohexyl), and —CH$_2$CH$_2$—O—CH$_3$.

In some embodiments of Formula VI, R$_{4B}$ is selected from the group consisting of hydrogen, alkyl, —CH$_2$Ph, —CH$_2$CH$_2$Ph, —CH$_2$CH$_2$—O-Ph, —CH$_2$CH$_2$—O—CH$_2$Ph, and —(CH$_2$)$_{2-6}$—O—(CH$_2$)$_{1-6}$ Ph, wherein Ph can be either unsubstituted or substituted with one or more substituents independently selected from the group consisting of halogen, hydroxy, alkyl, alkoxy, haloalkyl, and nitrile.

In some embodiments of Formula VI, R$_{5B}$ and R$_{6B}$ are independently selected from the group consisting of hydrogen, alkyl, phenyl, and phenylalkylenyl.

In some embodiments of Formula VI, R$_{5B}$ and R$_{6B}$ are independently selected from the group consisting of hydrogen, alkyl, cycloalkyl, cycloalkylalkylenyl, aryl, and arylalkylenyl.

In some embodiments of Formula VI, R$_{5B}$ and R$_{6B}$ are independently selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —(CH$_2$)$_{5-9}$CH$_3$, —CH$_2$CH$_2$CH(CH$_3$)$_2$, cyclopropyl, cyclopentyl, cyclohexyl, —CH$_2$-cyclopropyl, —CH$_2$-cyclopentyl, —CH$_2$-cyclohexyl, —(CH$_2$)$_{3-8}$—O—CH$_3$, —CH$_2$CH$_2$OCH$_3$, and —CH$_2$CH$_2$CH$_2$N(CH$_3$)$_2$.

In some embodiments of Formula VI, R$_{5B}$ and R$_{6B}$ are independently selected from the group consisting of hydrogen, alkyl, —CH$_2$Ph, —CH$_2$CH$_2$Ph, —CH$_2$CH$_2$—O-Ph, -Ph, —(CH$_2$)$_{3-8}$Ph, —(CH$_2$)$_{3-8}$—O-Ph, —CH$_2$CH$_2$—O—

CH$_2$Ph, —(CH$_2$)$_{3-8}$—O—CH$_2$Ph, and —(CH$_2$)$_{2-8}$—O—(CH$_2$)$_{1-4}$Ph, wherein the Ph group can be either unsubstituted or substituted with one or more substituents independently selected from the group consisting of halogen, hydroxy, alkoxy, alkyl, haloalkyl, cycloalkyl, and nitrile.

In some embodiments of Formulas VI, R$_{5B}$ and R$_{6B}$ are independently selected from the group consisting of hydrogen and —C(O)Oalkyl.

In some embodiments of Formula VI, R$_{5B}$ is alkyl and R$_{6B}$ is alkyl.

In some embodiments of Formula VI, R$_{5B}$ is C$_{1-8}$alkyl and R$_{6B}$ is C$_{1-8}$alkyl.

In some embodiments of Formula VI, R$_{5B}$ is C$_{1-4}$ alkyl and R$_{6B}$ is C$_{1-4}$ alkyl.

In some embodiments of Formula VI, R$_{5B}$ is —C(O)OC(CH$_3$)$_3$ and R$_{6B}$ is —C(O)OC(CH$_3$)$_3$.

In some embodiments of Formulas VI, R$_{5B}$ is hydrogen and R$_{6B}$ is hydrogen.

In some embodiments of Formulas VI, R$_{4B}$ is hydrogen; R$_{5B}$ is hydrogen; and R$_{6B}$ is hydrogen.

In some embodiments of Formula VI, X$_B$ is alkylene optionally interrupted by one or more —O— groups.

In some embodiments of Formula VI, X$_B$ is a C$_{2-12}$alkylene optionally interrupted by one or more —O— groups.

In some embodiments of Formula VI, X$_B$ is a C$_{2-8}$alkylene optionally interrupted by one or more —O— groups.

In some embodiments of Formula VI, X$_B$ is C$_{2-8}$ alkylene.
In some embodiments of Formula VI, X$_B$ is C$_{2-6}$ alkylene.
In some embodiments of Formula VI, X$_B$ is C$_{2-5}$ alkylene.

In some embodiments of Formula VI, X$_B$ is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$—O—CH$_2$CH$_2$—, —CH$_2$CH$_2$—O—CH$_2$CH$_2$—.

In some embodiments of Formula VI, X$_B$ is alkylene optionally interrupted by one or more —O— groups.

In some embodiments of Formula VI, X$_B$ is alkylene.

In some embodiments of Formula VI, X$_B$ is alkylene optionally interrupted by one or more —O— groups; R$_{5B}$ and R$_{6B}$ are independently selected from the group consisting of hydrogen and alkyl.

In some embodiments of Formula VI, X$_B$ is alkylene; R$_{5B}$ and R$_{6B}$ are independently selected from the group consisting of hydrogen and alkyl.

In some embodiments of Formula VI, X$_B$ is alkylene optionally interrupted by one or more —O— groups; R$_{5B}$ is alkyl; R$_{6B}$ is alkyl.

In some embodiments of Formula VI, X$_B$ is alkylene optionally interrupted by one or more —O— groups; R$_{5B}$ is hydrogen; and R$_{6B}$ is hydrogen.

In some embodiments of Formula VI, X$_B$ is alkylene; R$_{5B}$ is hydrogen; and R$_{6B}$ is hydrogen.

In some embodiments of Formula VI, X$_B$ is alkylene optionally interrupted by one or more —O— groups; R$_{4B}$ is hydrogen; R$_{5B}$ is hydrogen, and R$_{6B}$ is hydrogen.

In some embodiments of Formula VI, X$_B$ is alkylene; R$_{4B}$ is hydrogen; R$_{5B}$ is hydrogen, and R$_{6B}$ is hydrogen.

In some embodiments of Formula VI, the compound is present in the form of a salt. The salt is typically a pharmaceutically acceptable salt. Most commonly the salt is a hydrochloride or dihydrochloride salt.

The disclosure provides a method of inducing cytokine biosynthesis in an animal comprising administering to the animal an effective amount of a compound or salt selected from the group consisting of any one of the above embodiments of Formulas I-VI.

The disclosure provides a method of inducing IFN-alpha biosynthesis in an animal by administering to the animal an effective amount of a compound or salt selected from any one of the above embodiments of Formulas I— VI.

The disclosure provides a method of inducing IFN-gamma biosynthesis in an animal by administering to the animal an effective amount of a compound or salt selected from any one of the above embodiments of Formulas I— VI.

The disclosure provides a method of inducing TNF-alpha biosynthesis in an animal by administering to the animal an effective amount of a compound or salt selected from any one of the above embodiments of Formulas I— VI.

The disclosure provides a method of inducing IP-10 biosynthesis in an animal by administering to the animal an effective amount of a compound or salt selected from any one of the above embodiments of Formulas I— VI.

The disclosure also provides a method of treating a viral disease in an animal by administering to the animal an effective amount of a compound or salt selected from any one of the above embodiments of Formulas I— VI.

The disclosure also provides a method of treating a neoplastic disease in an animal by administering to the animal an effective amount of a compound or salt selected from any one of the above embodiments of Formulas I— VI.

Compounds and pharmaceutically acceptable salts of Formulas II-VI are preferred embodiments of the disclosure.

The disclosure also provides for compounds of the following Formula VII:

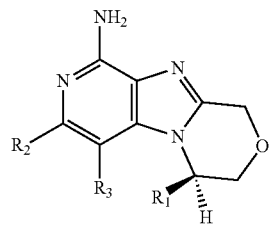

Formula VII wherein R$_1$, R$_2$, and R$_3$ are as defined in any one of the embodiments of Formula I above and pharmaceutically acceptable salts thereof.

The disclosure also provides for compounds of the following Formula VIII:

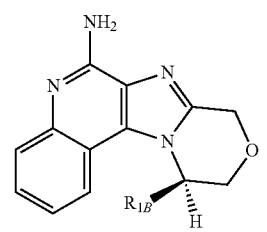

Formula VIII wherein R$_{1B}$ is as defined in any one of the embodiments of Formula VI above and pharmaceutically acceptable salts thereof.

The disclosure also provides for compounds of the following Formula IX:

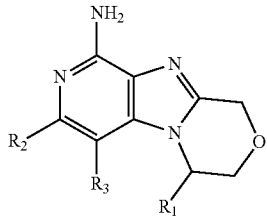

Formula IX wherein R₁, R₂, and R₃ are as defined in any one of the embodiments of Formula I above and pharmaceutically acceptable salts thereof.

The disclosure also provides for compounds of Formula X:

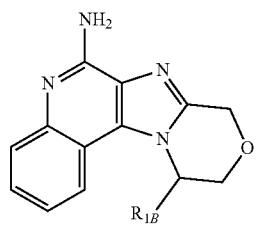

Formula X wherein $R_{1B}$ is as defined in any one of the embodiments of Formula VI above and pharmaceutically acceptable salts thereof.

The compounds of the disclosure may be synthesized by synthetic routes that include processes analogous to those well known in the chemical arts, particularly in light of the description contained herein. The starting materials are generally available from commercial sources such as Sigma-Aldrich Company (St. Louis, Mo.) or are readily prepared using methods well known to those of ordinary skill in the art (e.g., prepared by methods generally described in Louis F. Fieser and Mary Fieser, Reagents for Organic Synthesis, v. 1-26, Wiley, New York; Alan R. Katritsky, Otto Meth-Cohn, Charles W. Rees, Comprehensive Organic Functional Group Transformations, v 1-6, Pergamon Press, Oxford, England, (1995); Barry M. Trost and Ian Fleming, Comprehensive Organic Synthesis, v. 1-8, Pergamon Press, Oxford, England, (1991); or Beilsteins Handbuch der Organischen Chemie, 4, Aufl. Ed. Springer-Verlag, Berlin, Germany, including supplements (also available via the Beilstein online database)).

Specifically, the compounds of the disclosure can be prepared using any one of several standard methods for preparing guanidine containing compounds. Several standard methods are known to those of ordinary skill in the art for converting amino groups to guanidines (see Katritzky, *ARKIVOC*, 2005, iv, pages 49-87; Zhang, *Chem Commun*, 2015, 51, pages 254-265; Bernatowicz, *Journal of Organic Chemistry*, 1992, 57, pages 2497-2502). For example, amine compounds (such as those of Formulas XI, XII and XIII) can be reacted with pyrazole-1-carboxamidine hydrochloride (CAS Number 4023-02-3), or benzotriazole-1-carboxamidinium tosylate (CAS Number 163853-10-9), or triazole-1-carboxamidine hydrochloride (CAS Number 19503-26-5) to provide the compounds of the disclosure. As a further example, amine compounds (such as those of Formulas XI, XII and XIII) can be reacted with N,N'-bis-BOC-pyrazole-1-carboxamidine (CAS Number 152120-54-2) to form a di-Boc protected guanidine. The BOC protecting groups can be subsequently be removed using standard techniques such as treatment with acid to provide the compounds of the disclosure (see Bernatowicz, Tetrahedron Letters, 1993, 34, pages 3389-3392).

Amine compounds (such as those of Formulas XI, XII and XIII) can be reacted with an activated thiourea to provide the compounds of the disclosure (see Maryanoff, *Journal of Organic Chemistry*, 1986, 51, pages 1882-1884). As another example, amine compounds (such as those of Formulas XI, XII, and XII) can be reacted with a substituted carbodiimide compound to provide the compounds of the disclosure (e.g., N,N'-diisopropylcabodiimide [CAS Number 693-13-0], N,N'-dicyclohexylcarbodiimide [CAS Number 538-75-0], N-ethyl-N'(3-dimethylaminopropyl)carbodiimide [CAS Number 25952-53-8], 1,3-di-para-tolylcarbodiimide [CAS Number 726-42-1], 1,3-di-ortho-tolylcarbodiimide, etc.). As yet another example, amine compounds (such as those of Formulas XI, XII, and XIII) can be reacted with a substituted pyrazole-1-carboxamidine compound (such as for example N-propylpyrazole-1-carboxamidine hydrochloride, N-pentylpyrazole-1-carboxamidine hydrochloride, N-benzyl-1-carboxamidine hydrochloride, N-cyclopropylmethyl-1-carboxamidine hydrochloride, etc.) to provide the compounds of the disclosure [see Lee, *Bioorganic & Medicinal Chemistry Letters*, 2000, 10, pages 2771-2774; Lee, *Synthesis*, 1999, pages 1495-1499; and Examples 62-65 of International Patent Publication WO2005/051380 (Scobie)].

Intermediate amine compounds that can be converted into the guanidine compounds of the disclosure are shown in Formulas XI-XIII, wherein R₂, R₃, and X are as defined in any of the embodiments above.

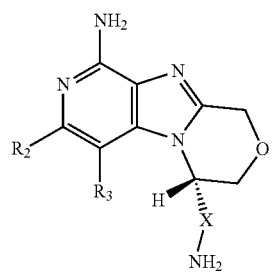

Formula XI

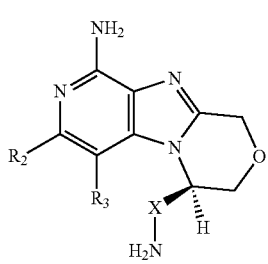

Formula XII

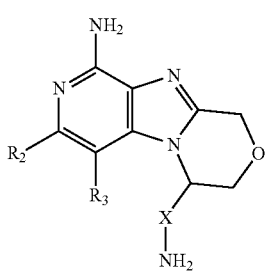

Formula XIII

Synthetic methods that are useful for the preparation of the intermediate amines of Formulas XI-XIII have been previously described in U.S. Pat. No. 8,034,938 (Griesgraber, see Reaction Schemes I-XI; parts A-I of Example 1; parts A-J of Example 2; Example 19; and Examples 67-71).

Asymmetric synthesis procedures can be used to preferably prepare compounds of the disclosure as single enantiomers. Alternatively, a racemic mixture of any compound of the disclosure (or synthetic precursor to any compound of the disclosure) can be resolved to provide the corresponding single enantiomers. For example, chiral chromatography (such as chiral HPLC) can be used to separate racemic mixtures into single enantiomers. Suitable chromatography columns are commercially available for example from Chiral Technologies, Inc., West Chester, Pa.

Single enantiomers of compounds or salts of Formulas I-VIII and XI-XII can be prepared with a percent enantiomeric excess (% ee) of >60% ee, >70% ee, >80% ee, >90% ee, >92% ee, >95% ee, >96% ee, >97% ee, >98% ee, >99% ee, >99.5% ee, >99.8% ee, or >99.9% ee.

Preferably single enantiomers of compounds or salts of Formulas I-VIII and XI-XII are prepared with a percent enantiomeric excess (% ee) of >90% ee.

More preferably single enantiomers of compounds or salts of Formulas I-VIII and XI-XII are prepared with a percent enantiomeric excess (% ee) of >95% ee.

Still more preferably single enantiomers of compounds or salts of Formulas I-VIII and XI-XII are prepared with a percent enantiomeric excess (% ee) of >98% ee.

Preferably single enantiomers of compounds or salts of Formula I are prepared with a percent enantiomeric excess (% ee) of >90% ee.

More preferably single enantiomers of compounds or salts of Formula I are prepared with a percent enantiomeric excess (% ee) of >95% ee.

Still more preferably single enantiomers of compounds or salts of Formula I are prepared with a percent enantiomeric excess (% ee) of >98% ee.

Preferably single enantiomers of compounds or salts of Formula II are prepared with a percent enantiomeric excess (% ee) of >90% ee.

More preferably single enantiomers of compounds or salts of Formula II are prepared with a percent enantiomeric excess (% ee) of >95% ee.

Still more preferably single enantiomers of compounds or salts of Formula II are prepared with a percent enantiomeric excess (% ee) of >98% ee.

Preferably single enantiomers of compounds or salts of Formula VI are prepared with a percent enantiomeric excess (% ee) of >90% ee.

More preferably single enantiomers of compounds or salts of Formula VI are prepared with a percent enantiomeric excess (% ee) of >95% ee.

Still more preferably single enantiomers of compounds or salts of Formula VI are prepared with a percent enantiomeric excess (% ee) of >98% ee.

In the preparation of the compounds of the disclosure it is understood by one of ordinary skill in the art that it may be necessary to protect a particular functional group while reacting other functional groups of an intermediate compound. The need for such protection will vary depending on the nature of the particular functional group and the conditions of the particular reaction step. A review of reactions for protecting and deprotecting functional groups can be found in T. W. Greene and P. G. M. Wuts, *Protective Groups in Organic Synthesis*, John Wiley & Sons, New York, USA, 1991.

Conventional methods and techniques of separation and purification can be used to isolate the IRM compounds used in the formulations of the disclosure. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

When a group (or substituent or variable) is present more than once in any Formula described herein, each group (or substituent or variable) is independently selected, whether explicitly stated or not.

Compounds or salts of the present disclosure may exist in different tautomeric forms, and it is understood that all such forms are expressly included within the scope of this disclosure. Specifically, it is understood that for compounds of Formulas I-X, all tautomers are expressly included (whether explicitly drawn or not).

Prodrugs of the disclosed compounds can also be prepared by attaching to the compounds a functional group that can be cleaved under physiological conditions. Typically a cleavable functional group will be cleaved in vivo by various mechanisms (such a through a chemical (e.g., hydrolysis) or enzymatic transformation) to yield a compound of the disclosure. A discussion of the use of prodrugs is provided by T. Higuchi and W. Stella. "Prodrugs as Novel Delivery Systems", vol. 14 of the ACS Symposium Series, and in Bioreversible Carriers in Drug Design, ed. Edward B. Roche, American Pharmaceutical Association and Pergamon Press, 1987.

For any of the compounds of Formula I presented herein, each one of the variables R, $R_1$, $R_2$, $R_3$, $R_4$, $R_5$, $R_6$, X in any of the Formula I embodiments can be combined with any one or more of the other variables in any of the Formula I embodiments, as would be understood by one of ordinary skill in the art. Each of the resulting combinations of variables is also an embodiment of the disclosure.

For any of the compounds of Formula II-V presented herein, each one of the variables R, $R_1$, $R_4$, $R_5$, $R_6$, n, X in any of the Formula II-V embodiments can be combined with any one or more of the other variables in any of the Formula II-V embodiments, as would be understood by one of ordinary skill in the art. Each of the resulting combinations of variables is also an embodiment of the disclosure.

For any of the compounds of Formula VI presented herein, each one of the variables $R_{1B}$, $R_{4B}$, $R_{5B}$, $R_{6B}$, $X_B$ in any of the Formula VI embodiments can be combined with any one or more of the other variables in any of the Formula VI embodiments, as would be understood by one of ordinary skill in the art. Each of the resulting combinations of variables is also an embodiment of the disclosure.

Pharmaceutical Compositions and Biological Activity

Pharmaceutical compositions of the disclosure are also contemplated. Pharmaceutical compositions of the disclosure contain a therapeutically effective amount of a compound or salt of the disclosure (described herein) in combination with a pharmaceutically acceptable carrier.

The exact amount of compound or salt used in a pharmaceutical composition of the disclosure will vary according to factors known to those of skill in the art, such as the physical and chemical nature of the compound or salt, the nature of the carrier, and the intended dosing regimen.

The exact amount of compound or salt used in a pharmaceutical composition of the disclosure will vary according to factors known to those of skill in the art, such as the physical and chemical nature of the compound or salt, the nature of the carrier, and the intended dosing regimen.

In some embodiments, the compositions of the disclosure will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In some embodiments, the compositions of the disclosure will contain sufficient active ingredient or prodrug to provide a dose of for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)×0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A pharmaceutical composition may contain a racemic or a non-racemic mixture of a compound or salt of the disclosure. For compositions containing a non-racemic mixture of a compound or salt of the disclosure, the non-racemic mixture can preferably have a percent enantiomeric excess (% ee) of >60% ee, >70% ee, >80% ee, >90% ee, >92% ee, >95% ee, >96% ee, >97% ee, >98% ee, >99% ee, >99.5% ee, >99.8% ee or >99.9% ee.

In some embodiments, the pharmaceutical composition contains a compound or salt of Formula I in >60% ee, >70% ee, >80% ee, >90% ee, >95% ee, >96% ee, >97% ee, >98% ee, >99% ee, >99.5% ee, >99.8% ee, or >99.9% ee.

In some embodiments, the pharmaceutical composition contains a compound or salt of Formula I in >90% ee.

In some embodiments, the pharmaceutical composition contains a compound or salt of Formula I in >95% ee.

In some embodiments, the pharmaceutical composition contains a compound or salt of Formula I in >98% ee.

In some embodiments, the pharmaceutical composition contains a compound or salt of Formula II in >60% ee, >70% ee, >80% ee, >90% ee, >95% ee, >96% ee, >97% ee, >98% ee, >99% ee, >99.5% ee, >99.8% ee, or >99.9% ee.

In some embodiments, the pharmaceutical composition contains a compound or salt of Formula II in >90% ee.

In some embodiments, the pharmaceutical composition contains a compound or salt of Formula II in >95% ee.

In some embodiments, the pharmaceutical composition contains a compound or salt of Formula II in >98% ee.

In some embodiments, the pharmaceutical composition contains a compound or salt of Formula VI in >60% ee, >70% ee, >80% ee, >90% ee, >92% ee, >95% ee, >96% ee, >97% ee, >98% ee, >99% ee, >99.5% ee, >99.8% ee, or >99.9% ee.

In some embodiments, the pharmaceutical composition contains a compound or salt of Formula VI in >90% ee.

In some embodiments, the pharmaceutical composition contains a compound or salt of Formula VI in >95% ee.

In some embodiments, the pharmaceutical composition contains a compound or salt of Formula VI in >98% ee.

A variety of dosage forms may be used to administer the compounds or salts of the disclosure to an animal. Dosage forms that can be used include, for example, tablets, lozenges, capsules, parenteral formulations, creams, ointments, topical gels, aerosol formulations, liquid formulations (e.g., aqueous formulation), transdermal patches, and the like. These dosage forms can be prepared with conventional pharmaceutically acceptable carriers and additives using conventional methods, which generally include the step of bringing the active ingredient into association with the carrier. A preferred dosage form has one or more of compounds or salts of the disclosure dissolved in an aqueous formulation.

Compounds or salts disclosed herein induce the production of certain cytokines in experiments performed according to the description of the Examples. These results indicate that the compounds or salts are useful for enhancing the immune response in a number of different ways, making them useful in the treatment of a variety of disorders.

The compounds or salts described herein can be administered as the single therapeutic agent in the treatment regimen, or the compounds or salts described herein may be administered in combination with one another or with other active agents, including additional immune response modifiers, antivirals, antibiotics, proteins, peptides, oligonucleotides, antibodies, etc.

Compounds or salts described herein induce the production of cytokines (e.g., IFN-alpha, IFN-gamma, TNF-alpha, IP-10) in experiments performed according to the tests set forth below. These results indicate that the compounds of the disclosure or salts are useful for activating the immune response in a number of different ways, rendering them useful in the treatment of a variety of disorders. As such, the compounds or salts of the disclosure (compounds or salts of Formulas I-X) are agonists of cytokine biosynthesis and production, particularly agonists of IFN-alpha, IFN-gamma, TNF-alpha, and IP-10 cytokine biosynthesis and production.

It is believed that one way in which the compounds or salts of the disclosure can induce cytokine production is through the activation of Toll-like receptors (TLRs) in the immune system, particularly TLR-7 and/or TLR-8, however other mechanisms may be involved. It is believed that in the immune system pathways (i.e. mechanisms) for cytokine induction, the compounds or salts of the disclosure primarily act as agonists of TLR-7 and/or TLR-8, however other pathways or activities may be involved.

Administration of the compounds or salts described herein can induce the production of interferon-alpha (IFN-alpha), interferon-gamma (IFN-gamma), tumor necrosis factor-alpha (TNF-alpha), and IP-10 in cells. Cytokines whose biosynthesis can be induced by compounds or salts of the disclosure include IFN-alpha, IFN-gamma, TNF-alpha, IP-10, and a variety of other cytokines. Among other effects, these cytokines can inhibit virus production and tumor cell growth, making the compounds or salts useful in the treatment of viral diseases and neoplastic diseases. Accordingly, the disclosure provides a method of inducing cytokine biosynthesis in an animal by administering an effective amount of a compound or salt of the disclosure to the animal. The animal to which the compound or salt is administered for induction of cytokine production may have one or more diseases, disorders, or conditions described below, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. In addition, the compounds or salts may cause proliferation and differentiation of B-lymphocytes.

Conditions for which compounds or salts or compositions identified herein may be used as treatment include, but are not limited to:

Viral diseases such as, for example, diseases resulting from infection by an adenovirus, a herpes virus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus, avian influenza), a paramyxovirus (e.g., parainfluenzavirus, mumps virus, measles virus, and respiratory syncytial virus (RSV), a coronavirus (e.g., SARS), a papovavirus (e.g., papillomaviruses, such as those that cause genital warts, common warts, or plantar warts), hepadnavirus (e.g., hepatitis B virus), a flavivirus (e.g., hepatitis C virus or Dengue virus), or a retrovirus (e.g., a lentivirus such as HIV), ebolavirus;

Neoplastic diseases such as bladder cancer, cervical dysplasia, actinic keratosis, basal cell carcinoma, cutaneous T-cell lymphoma, mycosis fungoides, Sezary Syndrome, HPV associated head and neck cancer (e.g., HPV positive oropharyngeal squamous cell carcinoma), Kaposi's sarcoma, melanoma, squamous cell carcinoma, renal cell carcinoma, acute myeloid leukemia, chronic myeloid leukemia, chronic lymphocytic leukemia, multiple myeloma, Hodgkin's lymphoma, non-Hodgkin's lymphoma, B-cell lymphoma, hairy cell leukemia, esophageal cancer, and other cancers;

$T_H2$-mediated atopic diseases such a atopic dermatitis or eczema, eosinophilia, asthma, allergy, allergic rhinitis, and Ommen's syndrome;

Diseases associated with wound repair, such as, for example, inhibition of keloid formation and other types of scarring (e g, enhancing wound healing, including chronic wounds); Parasitic diseases including but not limited to malaria, leishmaniasis, cryptosporidiosis, toxoplasmosis, and trypanosome infection.

In addition, a compound, salt, or composition described herein may be used as a vaccine adjuvant for use in conjunction with any material that increases either humoral and/or cell mediated immune responses, such as, for example, tumor antigens (e.g., MAGE-3, NY-ESO-1); live viral, bacterial, or parasitic immunogens; inactivated viral, protozoal, fungal, or bacterial immunogens; toxoids; toxins; polysaccharides; proteins; glycoproteins; peptides; cellular vaccines; DNA vaccines; autologous vaccines; recombinant proteins; and the like.

Examples of vaccines that can benefit from use of a compound, salt, or composition identified herein as a vaccine adjuvant include BCG vaccine, cholera vaccine, plague vaccine, typhoid vaccine, haepatitis A vaccine, hepatitis B vaccine, hepatitis C vaccine, influenza A vaccine, influenza B vaccine, parainfluenza vaccine, polio vaccine, rabies vaccine, measles vaccine, mumps vaccine, rubella vaccine, yellow fever vaccine, tetanus vaccine, diphtheria vaccine, hemophilus influenza b vaccine, tuberculosis vaccine, meningococcal and pneumococcal vaccines, adenovirus vaccine, HIV vaccine, chicken pox vaccine, cytomegalovirus vaccine, dengue vaccine, feline leukemia vaccine, fowl plague vaccine, HSV-1 vaccine and HSV-2 vaccine, hog cholera vaccine, Japanese encephalitis vaccine, respiratory syncytial virus vaccine, rotavirus vaccine, papilloma virus vaccine, yellow fever vaccine, ebola virus vaccine.

Compounds, salts, or compositions identified herein may be particularly useful as vaccine adjuvants when used in conjunction with tumor antigens associated with colorectal cancer, head and neck cancer, breast cancer, lung cancer and melanoma.

Compounds, salts, or compositions identified herein may be particularly useful in individuals having compromised immune function. For example, compounds, salts, or compositions may be used for treating opportunistic infections and tumors that occur after suppression of cell mediated immunity in, for example, transplant patients, cancer patients, and HIV patients.

One or more of the above diseases or types of diseases, for example, a viral disease or neoplastic disease may be treated in an animal in need thereof (having the disease) by administering a therapeutically effective amount of a compound, salt, or composition to the animal.

An animal may also be vaccinated by administering an effective amount of a compound, salt, or composition described herein as a vaccine adjuvant. In one embodiment, a method of vaccinating an animal includes administering an effective amount of a compound, salt, or composition described herein to the animal as a vaccine adjuvant. The vaccine adjuvant can be co-administered with the material that increases one or more humoral and cell mediated immune responses by including each in the same composition. Alternatively, the vaccine adjuvant and the material that increases either humoral and/or cell mediated immune responses can be in separate compositions.

Compounds or salts or compositions identified herein may be particularly useful when an effective amount is administered to an animal to treat bladder cancer, cervical dysplasia, actinic keratosis, basal cell carcinoma, genital warts, herpes virus infection, or cutaneous T-cell lymphoma. For these conditions, administration of the compound, salt, or composition of the disclosure is preferably topical (i.e. applied directly to the surface of a tumor, a lesion, a wart, or an infected tissue, etc).

In one embodiment an effective amount of compound, salt, or composition described herein, such as an aqueous composition is administered into the bladder of an animal that has at least one tumor of the bladder by intravesical instillation (e.g., administration using a catheter).

An amount of a compound or salt effective to induce cytokine biosynthesis will typically cause one or more cell types, such as monocytes, macrophages, dendritic cells, and B-cells to produce an amount of one or more cytokines, such as, for example, IFN-alpha, IFN-gamma, TNF-alpha, and IP-10 that is increased (induced) over a background level of such cytokines. The precise dose will vary according to factors known in the art but is typically to be a dose of about 100 ng/kg to about 50 mg/kg, preferably about 10 µg/kg to about 5 mg/kg. In other embodiments, the amount can be, for example, from about 0.01 mg/m$^2$ to about 5.0 mg/m$^2$, (computed according to the Dubois method as described above) although in other embodiments the induction of cytokine biosynthesis may be performed by administering a compound or salt in a dose outside this range. In some of these embodiments, the method includes administering sufficient compound or salt or composition to provide a dose from about 0.1 mg/m$^2$ to about 2.0 mg/m$^2$ to the subject, for example, a dose of from about 0.4 mg/m$^2$ to about 1.2 mg/m$^2$.

A method of treating a viral infection in an animal and a method of treating a neoplastic disease in an animal can include administering an effective amount of at least one compound or salt described herein to the animal. An effective amount to treat or inhibit a viral infection can be an amount that will cause a reduction in one or more of the manifestations of viral infection, such as viral lesions, viral load, rate of virus production, and mortality as compared to untreated control animals. The precise amount that is effective for such treatment will vary according to factors known in the art but it is normally a dose of about 100 ng/kg to about 50 mg/kg, preferably about 10 µg/kg to about 5 mg/kg. An amount of a compound or salt effective to treat a neoplastic condition can be an amount that causes a reduction in tumor size or in the number of tumor foci. The precise amount will vary according to factors known in the art but is typically about 100 ng/kg to about 50 mg/kg, preferably about 10 µg/kg to about 5 mg/kg. In other embodiments, the amount is typically, for example, from about 0.01 mg/m$^2$ to about 5.0 mg/m$^2$, (computed according to the Dubois method as described above) although in some embodiments the induction of cytokine biosynthesis may be performed by administering a compound or salt in a dose outside this range. In some of these embodiments, the method includes administering sufficient compound or salt or composition to provide a dose from about 0.1 mg/m$^2$ to about 2.0 mg/m$^2$ to the subject, for example, a dose of from about 0.4 mg/m$^2$ to about 1.2 mg/m$^2$.

EMBODIMENTS

Embodiment 1 is a compound of Formula (I):

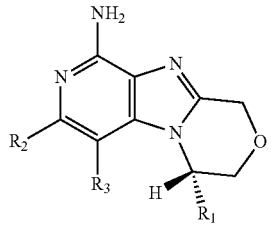

Formula I wherein:
$R_2$ and $R_3$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R groups;
R is selected from the group consisting of halogen, hydroxy, alkyl, alkoxy, haloalkyl, —C(O)Oalkyl, —C(O)OCH$_2$Ph, —C(O)Oaryl, amino, alkylamino, dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalky- enyl, heteroarylalkyleneoxy, and heteroaryloxy groups can be unsubstituted or substituted by one or more substituents independently selected from the group consisting of alkyl, alkoxy, halogen, haloalkyl, hydroxy, hydroxyalkylenyl, alkoxyalkylenyl, arylalkyleneoxy, cyano, amino, alkylamino, and dialkylamino;
$R_1$ is —X—N($R_4$)—C(=N—$R_5$)—N(H)$R_6$;
X is selected from the group consisting of alkylene, alkenylene, and alkynylene, wherein any of the alkylene, alkenylene, and alkynylene groups can be optionally interrupted by one or more —O— groups;
$R_4$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl, wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents independently selected from the group consisting of halogen, hydroxy, alkoxy, alkyl, haloalkyl, and nitrile;
$R_5$ and $R_6$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, benzyloxyalkylenyl, and —C(O)Oalkyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxy, alkoxy, alkyl, haloalkyl, cycloalkyl, nitrile, aryl, heteroaryl, and dialkylamino;
or a pharmaceutically acceptable salt thereof.

Embodiment 2 is the compound or salt of embodiment 1, wherein $R_2$ and $R_3$ are taken together to form a fused benzene ring, a fused pyridine ring, or a fused cyclohexene ring.

Embodiment 3 is the compound or salt of any one of the embodiments 1-2, wherein $R_2$ and $R_3$ are taken together to form a fused benzene ring, a fused pyridine ring, or a fused cyclohexene ring, and wherein the fused benzene ring, fused pyridine ring, or fused cyclohexene ring is either unsubstituted or substituted by one and only one R group.

Embodiment 4 is the compound or salt of any one of the embodiments 1-3, wherein $R_2$ and $R_3$ are taken together to form a fused benzene ring or a fused cyclohexene ring, and wherein the fused benzene ring, or fused cyclohexene ring is either unsubstituted or substituted by one and only one R group.

Embodiment 5 is the compound or salt of any one of the embodiments 1-3, wherein $R_2$ and $R_3$ are taken together to form a fused benzene ring or a fused pyridine ring, and wherein the fused benzene ring, or fused pyridine ring is either unsubstituted or substituted by one and only one R group.

Embodiment 6 is the compound or salt of any one of the embodiments 1-5, wherein R is selected from the group consisting of hydroxy, Br, F, Cl, —CF$_3$, —OCF$_3$, —O—C$_{1-6}$ alkyl, and —C$_{1-6}$ alkyl.

Embodiment 7 is the compound or salt of any one of the embodiments 1-5, wherein R is selected from the group consisting of hydroxy, Br, F, Cl, —CF$_3$, —OCH$_3$, —OCF$_3$, —OCH$_2$CH$_3$, —OCH(CH$_3$)$_2$, —CH$_3$, —CH$_2$CH$_3$, —CH$_2$CH$_2$CH$_3$, and —CH(CH$_3$)$_2$.

Embodiment 8 is the compound or salt of any one of the embodiments 1-5, wherein R is —C(O)OC$_{1-4}$ alkyl.

Embodiment 9 is the compound or salt of any one of the embodiments 1-5, wherein R is selected from the group consisting of —CO$_2$CH$_3$, —CO$_2$CH$_2$CH$_3$, —CO$_2$CH(CH$_3$)$_2$, —CO$_2$CH$_2$CH$_2$CH$_3$, —CO$_2$CH$_2$CH$_2$CH$_2$CH$_3$, —CO$_2$—CH$_2$Ph, and —CO$_2$CH$_2$CH(CH$_3$)$_2$.

Embodiment 10 is the compound or salt of any one of the embodiments 1-9, wherein R$_4$ is hydrogen, alkyl, or —CH$_2$Ph.

Embodiment 11 is the compound or salt of any one of the embodiments 1-10, wherein R$_4$ is hydrogen, C$_{1-8}$ alkyl, or —CH$_2$Ph.

Embodiment 12 is the compound or salt of any one of the embodiments 1-11, wherein R$_4$ is hydrogen or C$_{1-4}$ alkyl.

Embodiment 13 is the compound or salt of any one of the embodiments 1-9, wherein R$_4$ is selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —CH$_2$CH$_2$CH(CH$_3$)$_2$, cyclopentyl, cyclohexyl, —CH$_2$(cyclopentyl), —CH$_2$(cyclohexyl), and —CH$_2$CH$_2$—O—CH$_3$.

Embodiment 14 is the compound or salt of any one of the embodiments 1-9, wherein R$_4$ is selected from the group consisting of hydrogen, alkyl, —CH$_2$Ph, —CH$_2$CH$_2$Ph, —CH$_2$CH$_2$—O-Ph, —CH$_2$CH$_2$—O—CH$_2$Ph, and —(CH$_2$)$_{2-6}$—(CH$_2$)$_{1-6}$Ph, wherein Ph can be either unsubstituted or substituted with one or more substituents independently selected from the group consisting of halogen, hydroxy, alkyl, alkoxy, haloalkyl, and nitrile.

Embodiment 15 is the compound or salt of any one of the embodiments 1-14, wherein X is alkylene optionally interrupted by one or more —O— groups.

Embodiment 16 is the compound or salt of any one of the embodiments 1-15, wherein X is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$—O—CH$_2$CH$_2$—, —CH$_2$CH$_2$—O—CH$_2$CH$_2$.

Embodiment 17 is the compound or salt of any one of the embodiments 1-16, wherein R$_5$ and R$_6$ are independently selected from the group consisting of hydrogen, alkyl, phenyl, and phenylalkylenyl.

Embodiment 18 is the compound or salt of any one of the embodiments 1-17, wherein R$_5$ and R$_6$ are independently selected from the group consisting of alkyl, phenyl, and phenylalkylenyl.

Embodiment 19 is the compound or salt of any one of the embodiments 1-18, wherein R$_5$ is alkyl and R$_6$ is alkyl.

Embodiment 20 is the compound or salt of any one of the embodiments 1-19, wherein R$_5$ is C$_{1-8}$alkyl and R$_6$ is C$_{1-8}$ alkyl.

Embodiment 21 is the compound or salt of any one of the embodiments 1-20, wherein R$_5$ is C$_{1-4}$ alkyl and R$_6$ is C$_{1-4}$ alkyl.

Embodiment 22 is the compound or salt of any one of the embodiments 1-16, wherein R$_5$ and R$_6$ are independently selected from the group consisting of hydrogen, —CH$_3$, —CH$_2$CH$_3$, —CH(CH$_3$)$_2$, —CH$_2$CH$_2$CH$_3$, —CH$_2$CH$_2$CH$_2$CH$_3$, —CH$_2$CH(CH$_3$)$_2$, —C(CH$_3$)$_3$, —CH$_2$CH$_2$CH$_2$CH$_2$CH$_3$, —(CH$_2$)$_{5-9}$CH$_3$, —CH$_2$CH$_2$CH(CH$_3$)$_2$, cyclopropyl, cyclopentyl, cyclohexyl, —CH$_2$-cyclopropyl, —CH$_2$-cyclopentyl, —CH$_2$-cyclohexyl, —CH$_2$CH$_2$—O—CH$_3$, —(CH$_2$)$_{3-8}$—O—CH$_3$, and —CH$_2$CH$_2$CH$_2$N(CH$_3$)$_2$.

Embodiment 23 is the compound or salt of any one of the embodiments 1-16, wherein R$_5$ and R$_6$ are independently selected from the group consisting of hydrogen, alkyl, —CH$_2$Ph, —CH$_2$CH$_2$Ph, —CH$_2$CH$_2$—O-Ph, -Ph, —(CH$_2$)$_{3-8}$—O-Ph, —(CH$_2$)$_{3-8}$—O-Ph, —CH$_2$CH$_2$—O—CH$_2$Ph, —(CH$_2$)$_{3-8}$—O—CH$_2$Ph, and —(CH$_2$)$_{2-8}$—O—(CH$_2$)$_{1-4}$ Ph, wherein the Ph group can be either unsubstituted or substituted with one or more substituents independently selected from the group consisting of halogen, hydroxy, alkoxy, alkyl, haloalkyl, cycloalkyl, and nitrile.

Embodiment 24 is the compound or salt of any one of the embodiments 1-17, wherein R$_5$ is hydrogen and R$_6$ is hydrogen.

Embodiment 25 is the compound or salt of any one of the embodiments 1-17, wherein R$_4$ is hydrogen, R$_5$ is hydrogen, and R$_6$ is hydrogen.

Embodiment 26 is the compound or salt of any one of the embodiments 1-25, wherein the pharmaceutically acceptable salt is hydrochloride.

Embodiment 27 is the compound or salt of any one of the embodiments 1-25, wherein the pharmaceutically acceptable salt is dihydrochloride.

Embodiment 28 is a compound of Formula VI:

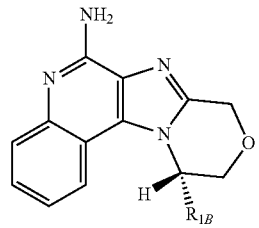

Formula VI wherein:

R$_{1B}$ is —X$_B$—N(R$_{4B}$)—C(=N—R$_{5B}$)—N(H)R$_{6B}$;

X$_B$ is selected from the group consisting of alkylene, alkenylene, and alkynylene, wherein the alkylene, alkenylene, and alkynylene groups can be optionally interrupted by one or more —O— groups;

R$_{4B}$ is selected from the group consisting of hydrogen, alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl, wherein any of the alkyl, arylalkylenyl, alkoxyalkylenyl, aryloxyalkylenyl, benzyloxyalkylenyl, aryl-(CH$_2$)$_{2-6}$—O-alkylenyl, and cycloalkylalkylenyl groups can be either unsubstituted or substituted with one or more substituents independently selected from the group consisting of halogen, hydroxy, alkoxy, alkyl, haloalkyl, and nitrile;

R$_{5B}$ and R$_{6B}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl, and —C(O)Oalkyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-(CH$_2$)$_{2-6}$—O-alkylenyl, and benzyloxyalkylenyl groups can be either unsubstituted or substituted with one or more substituents independently selected from the group consisting of halogen, hydroxy, alkoxy, alkyl, haloalkyl, cycloalkyl, nitrile, aryl, heteroaryl, and dialkylamino; or a pharmaceutically acceptable salt thereof.

Embodiment 29 is the compound or salt of embodiment 28, wherein R$_{4B}$ is hydrogen, alkyl, or —CH$_2$Ph.

Embodiment 30 is the compound or salt of any one of the embodiments 28-29, wherein $R_{4B}$ is hydrogen, $C_{1-8}$ alkyl, or —$CH_2Ph$.

Embodiment 31 is the compound or salt of any one of the embodiments 28-30, wherein $R_{4B}$ is hydrogen or $C_{1-4}$ alkyl.

Embodiment 32 is the compound or salt of embodiment 28, wherein $R_{4B}$ is selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$CH_2CH_2CH(CH_3)_2$, cyclopentyl, cyclohexyl, —$CH_2$(cyclopentyl), —$CH_2$(cyclohexyl), and —$CH_2CH_2$—O—$CH_3$.

Embodiment 33 is the compound or salt of embodiment 28, wherein $R_{4B}$ is selected from the group consisting of hydrogen, alkyl, —$CH_2Ph$, —$CH_2CH_2Ph$, —$CH_2CH_2$—O—Ph, —$CH_2CH_2$—O—$CH_2Ph$, and —$(CH_2)_{2-6}$—O—$(CH_2)_{1-6}$ Ph, wherein Ph can be either unsubstituted or substituted with one or more substituents independently selected from the group consisting of halogen, hydroxy, alkyl, alkoxy, and, nitrile.

Embodiment 34 is the compound or salt of any one of the embodiments 28-33, wherein $X_B$ is alkylene optionally interrupted by one or more —O— groups.

Embodiment 35 is the compound or salt of any one of the embodiments 28-34, wherein $X_B$ is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2$—O—$CH_2CH_2$—, —$CH_2CH_2$—O—$CH_2CH_2$.

Embodiment 36 is the compound or salt of any one of the embodiments 28-35, wherein $R_{5B}$ and $R_{6B}$ are independently selected from the group consisting of hydrogen, alkyl, phenyl, and phenylalkylenyl.

Embodiment 37 is the compound or salt of any one of the embodiments 28-36, wherein $R_{5B}$ and $R_{6B}$ are independently selected from the group consisting of alkyl, phenyl, and phenylalkylenyl.

Embodiment 38 is the compound or salt of any one of the embodiments 28-37, wherein $R_{5B}$ is alkyl and $R_{6B}$ is alkyl.

Embodiment 39 is the compound or salt of any one of the embodiments 28-38, wherein $R_{5B}$ is $C_{1-8}$alkyl and $R_{6B}$ is $C_{1-8}$alkyl.

Embodiment 40 is the compound or salt of any one of the embodiments 28-39, wherein $R_{5B}$ is $C_{1-4}$ alkyl and $R_{6B}$ is $C_{1-4}$ alkyl.

Embodiment 41 is the compound or salt of any one of the embodiments 28-35, wherein $R_{5B}$ and $R_{6B}$ are independently selected from the group consisting of alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxy, alkoxy, alkyl, haloalkyl, cycloalkyl, nitrile, aryl, heteroaryl, and dialkylamino.

Embodiment 42 is the compound or salt of any one of the embodiments 28-35, wherein $R_{5B}$ and $R_{6B}$ are independently selected from the group consisting of hydrogen, —$CH_3$, —$CH_2CH_3$, —$CH(CH_3)_2$, —$CH_2CH_2CH_3$, —$CH_2CH_2CH_2CH_3$, —$CH_2CH(CH_3)_2$, —$C(CH_3)_3$, —$CH_2CH_2CH_2CH_2CH_3$, —$(CH_2)_{5-9}$ $CH_3$, —$CH_2CH_2CH(CH_3)_2$, cyclopropyl, cyclopentyl, cyclohexyl, —$CH_2$-cyclopropyl, —$CH_2$-cyclopentyl, —$CH_2$-cyclohexyl, —$CH_2CH_2$—O—$CH_3$, —$(CH_2)_{3-8}$—O—$CH_3$, and —$CH_2CH_2CH_2N(CH_3)_2$.

Embodiment 43 is the compound or salt of any one of the embodiments 28-35, wherein $R_{5B}$ and $R_{6B}$ are independently selected from the group consisting of hydrogen, alkyl, —$CH_2Ph$, —$CH_2CH_2Ph$, —$CH_2CH_2$—O-Ph, -Ph, —$(CH_2)_{3-8}Ph$, —$(CH_2)_{3-8}$—O-Ph, —$CH_2CH_2$—O—$CH_2Ph$, —$(CH_2)_{3-8}$—O—$CH_2Ph$, and —$(CH_2)_{2-8}$—O—$(CH_2)_{1-4}Ph$, wherein the Ph group can be either unsubstituted or substituted with one or more substituents independently selected from the group consisting of halogen, hydroxy, alkoxy, alkyl, haloalkyl, cycloalkyl, and nitrile.

Embodiment 44 is the compound or salt of any one of the embodiments 28-35, wherein $R_{5B}$ is hydrogen and $R_{6B}$ is hydrogen.

Embodiment 45 is the compound or salt of any one of the embodiments 28-35, wherein $R_4$ is hydrogen, $R_{5B}$ is hydrogen, and $R_{6B}$ is hydrogen.

Embodiment 46 is the compound or salt of any one of the embodiments 28-45, wherein the pharmaceutically acceptable salt is hydrochloride.

Embodiment 47 is the compound or salt of any one of the embodiments 28-45, wherein the pharmaceutically acceptable salt is dihydrochloride.

Embodiment 48 is a method of inducing biosynthesis of IFN-alpha in an animal comprising administering an effective amount of a compound or salt of any one of the embodiments 1-47 to the animal.

Embodiment 49 is a method of inducing biosynthesis of IFN-gamma in an animal comprising administering an effective amount of a compound or salt of any one of the embodiments 1-47 to the animal.

Embodiment 50 is a method of inducing biosynthesis of TNF-alpha in an animal comprising administering an effective amount of a compound or salt of any one of the embodiments 1-47 to the animal.

Embodiment 51 is a method of inducing biosynthesis of IP-10 in an animal comprising administering an effective amount of a compound or salt of any one of the embodiments 1-47 to the animal.

Embodiment 52 is a method of inducing cytokine biosynthesis in an animal comprising administering an effective amount of a compound or salt of any one of the embodiments 1-47 to the animal.

Embodiment 53 is a pharmaceutical composition comprising a therapeutically effective amount of a compound or salt of embodiment 1-47 in combination with a pharmaceutically acceptable carrier.

Embodiment 54 is the compound or salt of any one of the embodiments 1-5, wherein R is selected from the group consisting of halogen, hydroxy, alkyl, alkoxy, haloalkyl, —C(O)Oalkyl, —C(O)OCH₂Ph, —C(O)Oaryl, amino, alkylamino, and dialkylamino.

Embodiment 55 is the compound or salt of any one of the embodiments 1-5, wherein R is selected from the group consisting of alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxy, hydroxyalkyl, alkoxyalkylenyl, arylalkyleneoxy, nitrile, amino, alkylamino, and dialkylamino.

Embodiment 56 is the compound or salt of any one of the embodiments 1-5, wherein R is selected from the group consisting of aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy.

Embodiment 57 is the compound or salt of any one of the embodiments 1-2, wherein R₂ and R₃ are taken together to form a fused benzene ring, a fused pyridine ring, or a fused cyclohexene ring, and wherein the fused benzene ring, fused pyridine ring, or fused cyclohexene ring is unsubstituted.

Embodiment 58 is the compound or salt of any one of the embodiments 1-9, 56, or 57, wherein R₁ is —X—N(H)—C(=N—H)—NH₂.

Embodiment 59 is the compound or salt of any one of the embodiments 28, wherein R₁ₐ is —X—N(H)—C(=N—H)—NH₂.

Embodiment 60 is the compound or salt of any one of the embodiments 1-16, 56, or 57, wherein R₅ and R₆ are independently selected from the group consisting of hydrogen and —C(O)Oalkyl.

Embodiment 61 is the compound or salt of any one of the embodiments 28-35, wherein R₅ₐ and R₆ₐ are independently selected from the group consisting of hydrogen and —C(O)Oalkyl.

Embodiment 62 is a compound selected from the group consisting of:
(11S)-1-{5-[6-amino-10,11-dihydro-8H-[1,4]oxazino[4',3':1,2]imidazo[4,5-c]quinolin-11-yl]pentyl}guanidine;
(11S)-1-{4-[6-amino-10,11-dihydro-8H-[1,4]oxazino[4',3':1,2]imidazo[4,5-c]quinolin-11-yl]butyl}guanidine;
(11S)-1-{3-[6-amino-10,11-dihydro-8H-[1,4]oxazino[4',3':1,2]imidazo[4,5-c]quinolin-11-yl]propyl}guanidine;
(11S)-1-{2-[6-amino-10,11-dihydro-8H-[1,4]oxazino[4',3':1,2]imidazo[4,5-c]quinolin-11-yl]ethyl}guanidine;
(11S)-1-{[6-amino-10,11-dihydro-8H-[1,4]oxazino[4',3':1,2]imidazo[4,5-c]quinolin-11-yl]methyl}guanidine;
or a pharmaceutically acceptable salt thereof.

Objects and advantages of the disclosure are further illustrated by the examples provided herein. The particular materials and amounts thereof recited in these examples, as well as other conditions and details, are merely illustrative and are not intended to be limiting. The person of ordinary skill in the art, after carefully reviewing the entirety of this disclosure, will be able to use materials and conditions in addition to those specifically described in the examples.

EXAMPLES

Example 1

(11S)-1-{3-[6-amino-10,11-dihydro-8H-[1,4]oxazino[4',3':1,2]imidazo[4,5-c]quinolin-11-yl]propyl}guanidine dihydrochloride

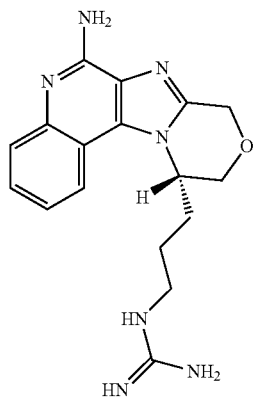

(11S)-11-(3-aminopropyl)-10,11-dihydro-8H-[1,4]oxazino[4',3':1,2]imidazo[4,5-c]quinolin-6-amine dihydrochloride (329 mg, 0.889 mmol, prepared according to Example 2 of U.S. Pat. No. 8,034,938) was dissolved 5 mL of anhydrous DMF and N,N'-bis-BOC-pyrazole-1-carboxamidine was added (303 mg, 0.978 mmol). After stirring for 2 days, the reaction mixture was then concentrated under reduced pressure. The resulting material was dissolved in 50 mL of dichloromethane and washed sequentially with water (2×) and brine. The organic layer was separated and then dried over sodium sulfate, filtered and concentrated under reduced pressure. Chromatography [SiO₂, chloroform/(5% methanol/chloroform saturated with NH₄OH) eluent] yielded 330 mg of (11S)-3-{3-[6-amino-10,11-dihydro-8H-[1,4]oxazino[4',3':1,2]imidazo[4,5-c]quinolin-11-yl]propyl}-1,2-(bis-tert-butoxtycarbonyOguanidine as a white solid.

The solid was dissolved in 5 mL of methanol and 5 mL of 1.2 M HCl in methanol was added. The reaction was heated with stirring at 70° C. After 5 hours, a second 5 mL portion of 1.2 M HCl in methanol was added to the reaction mixture and heating at 70° C. was continued overnight. The mixture was cooled and concentrated under reduced pressure to give a yellow solid. The solid was crystallized from methanol and acetonitrile to provide 128 mg of (11S)-1-{3-[6-amino-10,11-dihydro-8H-[1,4]oxazino[4',3':1,2]imidazo[4,5-c]quinolin-11-yl]propyl}guanidine dihydrochloride as white crystals. ¹H NMR (CD₃OD, 500 MHz) 8.19 (d, J=7.7 Hz, 1H) 7.85 (dd, J=1.0, 8.4 Hz, 1H), 7.78 (m, 1H), 7.70 (m, 1H), 5.22 (d, J=16.1 Hz, 1H), 5.11 (dt, J=2.2, 10.1 Hz, 1H), 5.04 (d, J=16.1 Hz, 1H), 4.45 (d, J=12.6 Hz, 1H), 4.20 (dd, J=2.0, 12.6 Hz, 1H), 3.26 (m, 2H), 2.24 (m, 1H), 2.03 (m, 2H), 1.81 (m, 1H).

Cytokine Induction in Human Cells

Whole blood was obtained from healthy human donors and collected by venipuncture into vacutainer tubes or syringes containing EDTA. Human peripheral blood mononuclear cells (PBMC) were purified from the whole blood by density gradient centrifugation. Histopaque 1077 (15 mL, Sigma, St. Louis, Mo.) was transferred to 6×50 mL sterile polypropylene conical tubes. The Histopaque was overlayed with 15-25 mL of blood diluted 1:2 in Hank's Balanced Salts Solution (HBSS) (Gibco, Life Technology, Grand Island N.Y.). The tubes were then centrifuged at 1370 rpm for 30 minutes at 20° C., with no brake (400×g, GH 3.8A Rotor).

The interface (buffy coat) containing the PBMC was collected and placed in a new sterile 50 mL conical polypropylene centrifuge tube. The PBMC were mixed with an equal volume of HBSS (about 20 mL from the interface and about 20 mL of HBSS), and then centrifuged at 1090 rpm, 10 min, 20° C., with brake (270×g, GH 3.8A Rotor). After completing centrifugation, the cells were resuspended in 2-3 mL ACK Red blood cell lysis buffer (ammonium chloride potassium solution, Gibco, Life Technology) and incubated for 2-5 minutes at 20° C. Next, HBSS (40 mL) was added to the cells, and the sample was centrifuged at 270×g for 10 min at 20° C. The supernatant was decanted, and the cell pellet was resuspended in 5 mL AIM V® Medium (Gibco, Life Technology). Cell aggregates and debris were removed by filtering the cell solution through a BD Falcon 70 micron nylon cell strainer (BD Biosciences, San Jose, Calif.).

The number of viable cells were determined by counting with a Miltenyi FACS instrument (Miltenyi Biotec Inc., San Diego, Calif.) or by using a hemacytometer. For determining cell viability with a hemacytometer, the cells were diluted 1/10 in 0.4% trypan blue and HBSS (specifically, 50 microliter of trypan blue+40 microliter of HBSS+10 microliter of cell solution were added to a microfuge tube and mixed). Ten microliters of the diluted cells were then applied to the hemacytometer, and the number of viable PBMC were determined by microscopy.

The PBMC sample was then resuspended in 96-well plates at a concentration of $8 \times 10^5$ cells/well in 0.1 mL of AIM-V medium. Each compound was solubilized in DMSO to create a 3 mM stock solution. The stock solution was then further diluted with AIM-V medium to prepare the serial dilutions. The diluted compound (100 microliters) was then transferred to the PBMCs to achieve final compound concentrations of 10, 1, 0.1, 0.01, 0.001, 0.0001 micromolar. The plates also had both positive and negative controls. The negative control wells contained only AIM-V medium with no example compound. The positive control wells contained imiquimod serially diluted to concentrations of 10, 1, 0.1, 0.01, 0.001, 0.0001 micromolar. The plates were then cultured at 37° C./5% $CO_2$ for 21-24 hrs. Cell-free supernatants were harvested by centrifuging the 96-well plates at 2100 rpm, 23° C. for 10 minutes. Approximately 160 microliter of the supernatant was then stored in a NUNC 96-well plate, covered with the compression cap and stored at −80° C. until the cytokine analysis was done.

IFN-alpha cytokine levels (pg/mL) were measured by ELISA (human IFN-α, pan specific, Mabtech, Cinncinnati, Ohio), IFN-gamma, TNF-alpha, and IP-10 cytokine levels (pg/mL) were measured by multiplex bead assay (magnetic beads, R & D Systems Minneapolis, Minn.) according to the manufacturer's instructions.

The data was analyzed to determine the minimum effective concentration (MEC) for each compound at which induction of a particular cytokine was observed in the assay. Specifically, the minimum effective concentration of each compound (micromolar) was determined as the lowest concentration of the compound that induced a measured cytokine response at a level (pictograms/mL) that was at least 2× greater than that observed with the negative control wells. The results are presented in Table 1.

TABLE 1

| Compound | MEC to Induce Cytokine (micromolar) | | | |
| --- | --- | --- | --- | --- |
| | IFN-alpha | IFN-gamma | TNF-alpha | IP-10 |
| Example 1 | 1.0 | 1.0 | NT | NT |

NT = not tested

The complete disclosures of the patents, patent documents, and publications cited herein are incorporated by reference in their entirety as if each were individually incorporated. Various modifications and alterations to this invention will become apparent to those of ordinary skill in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

I claim:
1. A compound of the Formula (I):

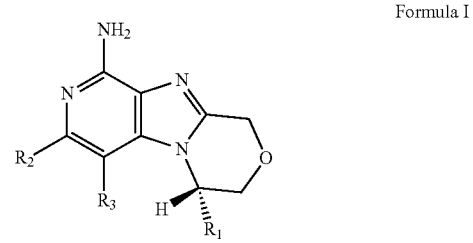

Formula I wherein:
$R_2$ and $R_3$ are taken together to form a fused benzene ring, a fused pyridine ring, a fused cyclohexene ring, or a fused tetrahydropyridine ring; wherein the fused benzene ring, fused pyridine ring, fused cyclohexene ring, or fused tetrahydropyridine ring is either unsubstituted or substituted by one or more R groups;
R is selected from the group consisting of halogen, hydroxy, alkyl, alkoxy, haloalkyl, $OCF_3$, —C(O)Oalkyl, —C(O)$OCH_2$Ph, —C(O)Oaryl, amino, alkylamino, dialkylamino, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy, wherein the alkyl, aryl, arylalkylenyl, aryloxyalkylenyl, arylalkyleneoxy, aryloxy, heteroaryl, heteroarylalkylenyl, heteroaryloxyalkyenyl, heteroarylalkyleneoxy, and heteroaryloxy groups can be unsubstituted or substituted by one or more substituents independently selected from the group consisting of alkyl, alkoxy, halogen, haloalkyl, hydroxy, hydroxyalkylenyl, alkoxyalkylenyl, arylalkyleneoxy, nitrile, amino, alkylamino, and dialkylamino;
$R_1$ is —X—N($R_4$)—C(=N—$R_5$)—N(H)$R_6$;
X is selected from the group consisting of alkylene, alkenylene, and alkynylene, wherein any of the alkylene, alkenylene, and alkynylene groups can be optionally interrupted by one or more —O— groups;
$R_4$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl;

wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents independently selected from the group consisting of halogen, hydroxy, alkyl, alkoxy, haloalkyl, and nitrile;

$R_5$ and $R_6$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, benzyloxyalkylenyl, and —C(O)Oalkyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxy, alkoxy, alkyl, haloalkyl, cycloalkyl, nitrile, aryl, heteroaryl, and dialkylamino;

or a pharmaceutically acceptable salt thereof.

2. The compound or salt of claim 1, wherein $R_2$ and $R_3$ are taken together to form a fused benzene ring, a fused pyridine ring, or a fused cyclohexene ring, and the fused benzene ring, fused pyridine ring, or fused cyclohexene ring is either unsubstituted or substituted by one and only one R group.

3. The compound or salt of claim 1, wherein $R_4$ is hydrogen.

4. The compound or salt of claim 1, wherein X is alkylene optionally interrupted by one or more —O— groups.

5. The compound or salt of claim 1, wherein X is alkylene.

6. The compound or salt of claim 1, wherein X is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2$—O—$CH_2CH_2$— and, —$CH_2CH_2$—O—$CH_2CH_2$—.

7. The compound or salt of claim 1, wherein R is selected from the group consisting of hydroxy, Br, F, Cl, —$CF_3$, —$OCF_3$, —O—$C_{1-6}$alkyl, and —$C_{1-6}$alkyl.

8. The compound or salt of claim 1, wherein $R_5$ and $R_6$ are independently selected from the group consisting of hydrogen, alkyl, phenyl, and phenylalkylenyl.

9. The compound or salt of claim 1, wherein $R_5$ and $R_6$ are independently selected from the group consisting of alkyl, phenyl, and phenylalkylenyl.

10. The compound or salt of claim 1, wherein $R_5$ is alkyl and $R_6$ is alkyl.

11. The compound or salt of claim 1, wherein $R_5$ is hydrogen and $R_6$ is hydrogen.

12. The compound or salt of claim 1, wherein $R_4$ is hydrogen, $R_5$ is hydrogen, and $R_6$ is hydrogen.

13. A compound of the Formula VI:

Formula VI wherein:

$R_{1B}$ is —$X_B$—N($R_{4B}$)—C(N—$R_{5B}$)—N(H)$R_{6B}$;

$X_B$ is selected from the group consisting of alkylene, alkenylene, and alkynylene, wherein the alkylene, alkenylene, and alkynylene groups can be optionally interrupted by one or more —O— groups;

$R_{4B}$ is selected from the group consisting of hydrogen, alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl;

wherein any of the alkyl, arylalkylenyl, alkoxyalkylenyl, aryloxyalkylenyl, benzyloxyalkylenyl, aryl-$(CH_2)_{2-6}$—O-alkylenyl, and cycloalkylalkylenyl groups can be either unsubstituted or substituted with one or more substituents independently selected from the group consisting of halogen, hydroxy, alkyl, alkoxy, haloalkyl, and nitrile;

$R_{5B}$ and $R_{6B}$ are independently selected from the group consisting of hydrogen, alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, benzyloxyalkylenyl, and —C(O)Oalkyl; wherein any of the alkyl, cycloalkyl, aryl, arylalkylenyl, aryloxyalkylenyl, heteroaryl, heteroarylalkylenyl, heteroaryloxyalkylenyl, cycloalkylalkylenyl, aryl-$(CH_2)_{2-6}$—O-alkylenyl, and benzyloxyalkylenyl groups can be either unsubstituted or substituted with one or more substituents independently selected from the group consisting of halogen, hydroxy, alkoxy, alkyl, haloalkyl, cycloalkyl, nitrile, aryl, heteroaryl, and dialkylamino;

or a pharmaceutically acceptable salt thereof.

14. The compound or salt of claim 13, wherein $R_{4B}$ is hydrogen.

15. The compound or salt of claim 13, wherein $X_B$ is alkylene optionally interrupted by one or more —O— groups.

16. The compound or salt of claim 13, wherein $X_B$ is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$—, —$CH_2$—O—$CH_2CH_2$— and, —$CH_2CH_2$—O—$CH_2CH_2$—.

17. The compound or salt of claim 13, wherein $R_{5B}$ and $R_{6B}$ are independently selected from the group consisting of hydrogen, alkyl, phenyl, phenylalkylenyl.

18. The compound or salt of claim 13, wherein $R_{5B}$ and $R_{6B}$ are independently selected from the group consisting of alkyl, phenyl, and phenylalkylenyl.

19. The compound or salt of claim 13 wherein $R_{5B}$ is alkyl and $R_{6B}$ is alkyl.

20. The compound or salt of claim 13, wherein $R_{5B}$ is hydrogen and $R_{6B}$ is hydrogen.

21. The compound or salt of claim 13, wherein $R_{4B}$ is hydrogen, $R_{5B}$ is hydrogen, and $R_{6B}$ is hydrogen.

22. A method of inducing biosynthesis of IFN-alpha in an animal comprising administering an effective amount of a compound or salt of claim 1 to the animal.

23. A pharmaceutical composition comprising a therapeutically effective amount of a compound or salt of claim 1 in combination with a pharmaceutically acceptable carrier.

* * * * *